United States Patent [19]
Marcadis et al.

[11] Patent Number: 5,197,952
[45] Date of Patent: Mar. 30, 1993

[54] AUTO-INFLATING CATHETER CUFF

[75] Inventors: Stuart J. Marcadis, Wyoming; James H. DeVries, Grand Rapids, both of Mich.

[73] Assignee: DLP, Inc., Grand Rapids, Mich.

[21] Appl. No.: 537,566

[22] Filed: Jun. 13, 1990

[51] Int. Cl.$^5$ .............................................. A61M 29/00
[52] U.S. Cl. ................................ 604/96; 604/98; 606/194
[58] Field of Search .............................. 604/96–101; 606/191, 194; 128/207.15

[56] References Cited

U.S. PATENT DOCUMENTS

| | | | |
|---|---|---|---|
| 3,394,705 | 7/1968 | Abramson | 128/349 |
| 3,402,717 | 9/1968 | Doherty . | |
| 3,467,101 | 9/1969 | Fogarty et al. | 606/194 |
| 3,915,171 | 10/1975 | Shermeta | 604/101 |
| 3,983,879 | 10/1976 | Todd | 128/349 |
| 4,029,104 | 6/1977 | Kerber | 604/96 |
| 4,290,428 | 9/1981 | Durand . | |
| 4,301,803 | 11/1981 | Handa et al. | 128/658 |
| 4,323,071 | 4/1982 | Simpson . | |
| 4,439,186 | 3/1984 | Kuhl . | |
| 4,441,495 | 4/1984 | Hicswa | 128/325 |
| 4,464,175 | 8/1984 | Altman | 604/99 |
| 4,484,579 | 11/1984 | Meno et al. . | |
| 4,496,345 | 1/1985 | Hasson | 604/103 |
| 4,535,757 | 8/1985 | Webster, Jr. | 604/104 |
| 4,573,966 | 3/1986 | Weikl et al. | 604/53 |
| 4,648,384 | 3/1987 | Schmukler . | |
| 4,689,041 | 8/1987 | Corday | 604/53 |
| 4,723,936 | 2/1988 | Buchbinder et al. | 604/96 |
| 4,751,924 | 6/1988 | Hammerschmidt | 128/207 |
| 4,771,777 | 9/1988 | Horzewski | 128/344 |
| 4,811,737 | 3/1989 | Rydell | 606/194 |
| 4,821,722 | 4/1989 | Miller et al. | 604/96 |
| 4,848,344 | 7/1989 | Sos | 128/344 |
| 4,850,969 | 7/1989 | Jackson | 604/96 |
| 4,994,033 | 2/1991 | Shockey et al. | 604/96 |
| 5,021,045 | 6/1991 | Buckberg et al. . | |
| 5,033,998 | 7/1991 | Corday et al. . | |

OTHER PUBLICATIONS

Retrograde Perfusion of the Coronary Sinus for Direct Vision Aortic Surgery, Gott et al; Surgery, Gunecology & Obstetrics, Mar. 1957, pp. 319–328.

An Improved Coronary Artery Perfusion Cannula, King, Chir; J. Thoracic and Cardiovascular Surgery, May 1963, p. 668.

Retrograde Coronary Capillary Perfusion for Prevention and Reversal of Cardiogenic Shock in Experimental Myocardial Infarction, Carabello et al, The Annals of Thoracic Surgery, May 1976, vol. 21, No. 5, pp. 405–411.

Synchronized Retropuerfusin of Coronary Veins for Circulatory Support of Jeopardized Ischemic Myocardium, Farcot et al, The Emerican Journal of Cardiology, Jun. 1978, vol. 41, pp. 1191–1201.

Retrograde Coronary Sinus Perfusion: A Safe Alternative for Ensuring Cardioplegic Delivery in Aortic Valve Surgery, Menasche et al, The Annals of Thoracic Surgery, Dec. 1982, vol. 82, vol. 34, Nov. 6, pp. 647–658.

Myocardial Protection by Retrograde Cardioplegia: Coronary Sinus and Right Atrial Methods, Chitwood, Cardiac Surgery: State of the Art Reviews, Feb. 1988, vol. 2, No. 2, pp. 197–217.

Primary Examiner—C. Fred Rosenbaum
Assistant Examiner—Ronald K. Stright, Jr.
Attorney, Agent, or Firm—Barnes, Kisselle, Raisch, Choate, Whittemore & Hulbert

[57] ABSTRACT

A perfusion catheter for use in open heart surgery having an inflatable cuff adjacent the distal end in communication with the lumen of the cathether to self-inflate when perfusion liquid is introduced into the lumen. A reinforcing spine is installed at the cuff area to lend stiffness to the distal end. Flow through passsages in the cuff prevent stagnation and also permit pressure monitoring of the cuff pressure as well as pressure at the distal end of the catheter. An introducer shaft is provided to abut a plug in the lumen, the plug serving to shunt flow through the cuff and also to allow the introducer to apply pressure to the distal end of the catheter when the distal end is being projected into a body organ.

12 Claims, 2 Drawing Sheets

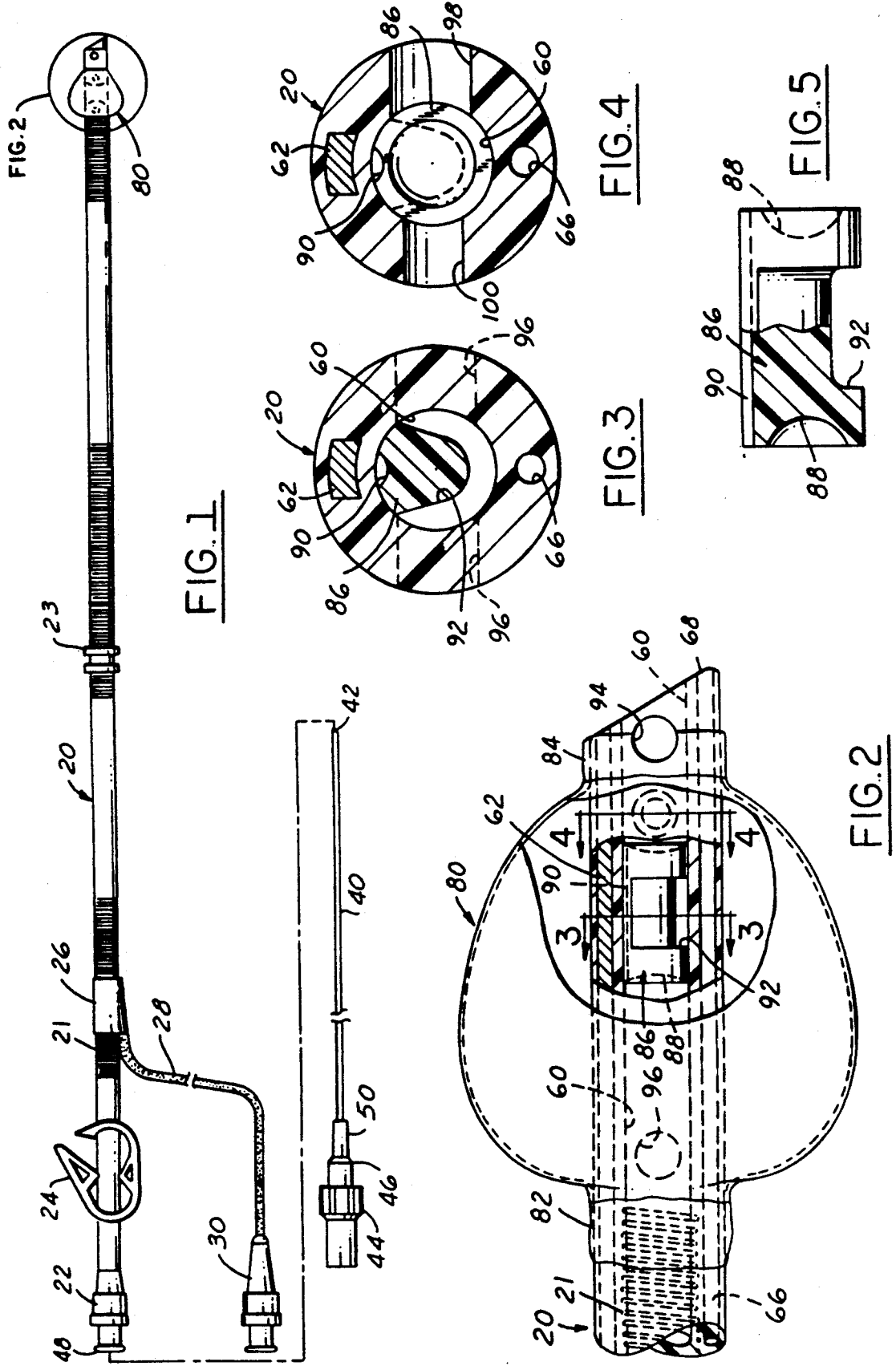

AUTO-INFLATING CATHETER CUFF

FIELD OF INVENTION

Cardioplegic catheter for use in open heart surgery and with self-inflating retention cuff.

BACKGROUND AND OBJECTS OF THE INVENTION

In use of catheters for introduction into a body cavity, a process called catheterization, it is common in some instances to include on the catheter itself an inflatable balloon or "cuff" which is inflated after introduction of the catheter to prevent accidental retraction or rejection of the catheter. It is usual to inflate the cuff from an outside source of air as, for example, a bulb pump. Representative of the prior art in this field is a U.S. Pat. No. 4,573,966 to Weikl et al.

The present invention is directed to a self-inflating cuff which can be used when the catheter is utilized for perfusion of liquid into a body cavity. One known means of accomplishing this inflation is to provide the catheter with an inflatable cuff surrounding the outside of the catheter spaced from the distal end. Openings into the cuff from the lumen are provided spaced axially of the lumen, and the sides of distal end of the catheter are provided with a plurality of openings for outflow of the perfusion liquid. The end of the lumen within the cuff is closed off and the openings are designed such that there will be a pressure in the lumen which will exert on the interior of the cuff to cause inflation.

It is an object of the invention to provide an improved self-inflating cuff which reduces stagnation of inflating media in the cuff and reduces the pressure drop across the cuff. It is a further object to provide an optional axial vent which prevents stagnation in the body of the catheter under the cuff. A further object is to provide a reinforcement to prevent unintentional collapse of the catheter in the cuff area. Pressure monitoring is important in the use of a perfusion function and an object is also to allow monitoring of the cuff pressure as well as the vessel pressure.

Pressure that approximates the intra-vessel condition in normal operation will also register cuff pressure. However, should the pressure monitor show an increase as might occur if the distal end of the catheter is inadvertently occluded, this would indicate undue pressure in the cuff and require immediate attention of the monitoring personnel. Other objects include a lumen plug with a design to assist in introducing the distal end of the catheter into a vessel.

Other objects and features of the invention will be apparent in the following description and claims in which the invention is described together with details to enable persons skilled in the art to practice the invention, all in connection with the best mode presently contemplated for the invention.

BRIEF DESCRIPTION OF THE DRAWINGS

DRAWINGS accompany the disclosure, and the various views thereof may be briefly described as:

FIG. 1, an elevation of a perfusion catheter with a pressure monitor tube and an introducer stylet.

FIG. 2, an enlarged portion partially in section of the cuff area of FIG. 1 enclosed in the circle.

FIG. 3, a sectional view on line 3—3 of FIG. 2.

FIG. 4, a sectional view on line 4—4 of FIG. 2.

FIG. 5, a sectional view of a plug used in the lumen of the catheter.

BRIEF DESCRIPTION OF THE INVENTION

Figure 6:
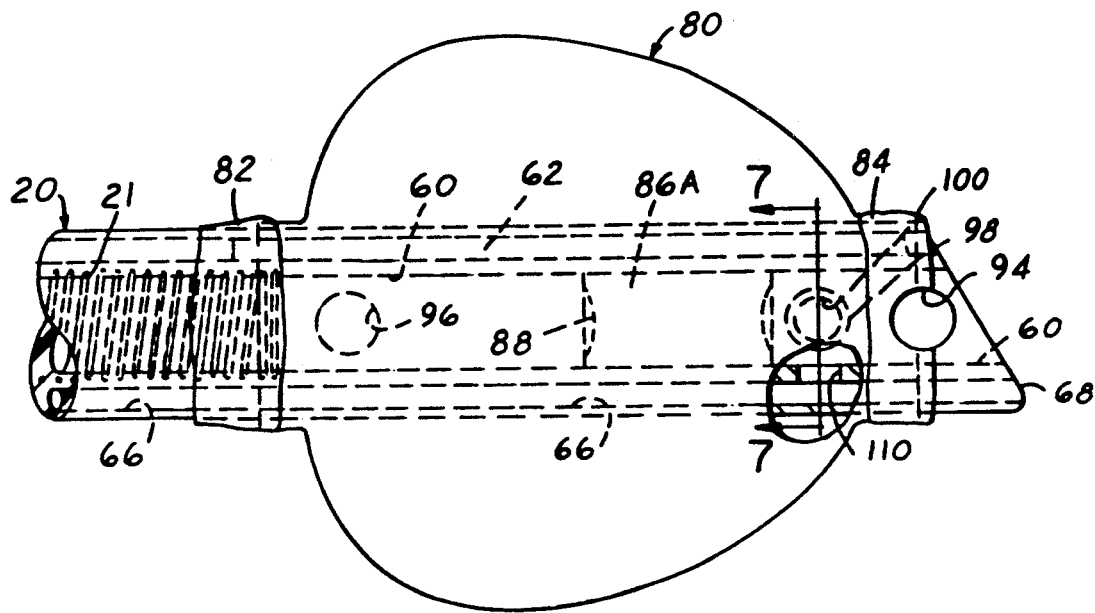
FIG. 6, a modification illustrating a pressure monitor port in the lumen for the cuff pressure.

A perfusion catheter having a distal end for introduction into the cavity of a body organ, as, for example, introducing cardioplegic liquid into a heart organ, which has a lumen blocked at an area of the distal end by a plug, the area being surrounded by an inflatable cuff. The interior of the cuff is in communication with the lumen to allow flow of liquid into and out of the cuff with a sufficient restriction at the distal end of the lumen to create an inflating pressure in the cuff when perfusion liquid is directed through the catheter. A reinforcing spine overlies the cuff area to resist kinking. An introducer shaft projectable into the catheter abuts a recess in the plug to allow pressure to be applied to the distal end during the introducing phase.

DETAILED DESCRIPTION OF THE INVENTION AND THE MANNER OF AND PROCESS OF USING IT

The catheter to be described is frequently used in the introduction of cardioplegic fluid (cooling fluid) into a heart at the beginning of and during an open heart surgical operation. In this procedure, it is important not only that the catheter remain in place but that a means be provided to prevent the cardioplegic solution from leaking around the catheter. Thus the use of the inflatable retention cuff is indicated to provide a seal within the heart. It is also important that a surgeon or a perfusionist be able to monitor the pressure in the heart cavity receiving the cardioplegic liquid. Monitoring pressure in the inflatable cuff is also important in instances where cuff pressures may increase significantly due to the tip of the catheter being inadvertently occluded during manipulation of the heart while delivering in the cardioplegic solution.

WITH REFERENCE TO THE DRAWINGS, in FIG. 1 an elevation of the catheter assembly is illustrated. The catheter body 20 is formed of a flexible plastic material with a reinforcing coiled spring 21 embedded in the wall of the plastic. A connector hub 22 at the proximal end is used to connect the catheter to a source of liquid in the use of the catheter for infusion. A slip ring 23 serves to aid in the manipulation of the catheter. A close-off snap-lock 24 is provided for use in a closing of the catheter. A band 26 closes the introduction of a pressure monitoring tube 28 which also has a connector hub 30.

Also, in FIG. 1, an introducer shaft 40 has a blunt distal end 42 and a hub 44 with a first cylindrical section 46 to abut the end 48 of hub 22 and a second tapered section 50. This section 50 is dimensioned to move into the end 48 of hub 22 in a slip-lock relationship useful in the introduction of the catheter into a body organ as will be later described.

Looking now at FIG. 2, an enlarged area of the distal end of the catheter is shown, partially in section, The catheter has a lumen 60 extending from the proximal to the distal end. A spine element 62 rigid to semi-rigid, is inserted off-center into the wall of the catheter tube at the distal end as shown in sectional views FIGS. 3 and 4. The spine element 62 is extended from close to the distal end back into the reinforcing coils spring area to unify the anti-kink characteristics of the distal end.

The pressure monitoring tube 28 joins with an incorporated passage 66 in the catheter tube wall, this passage being open at 68 to the distal end of the catheter.

Turning now to the inflatable retention cuff 80 shown in FIGS. 1 and 2, the cuff, formed of relatively thin flexible membrane that will retain the inflationary fluid during use, is enlarged at one end and tapered down to the distal end. This cuff compresses, deflates entirely, when the distal end of the catheter is introduced to the body organ.

The cuff 80 has two sleeve ends 82,84 which are snugged and sealed around the tube 20 at each end of the cuff. In the lumen 60 between the ends of the cuff 80 is inserted a lumen plug 86 which is cylindrical in basic shape and symmetrical. Each end has a locator recess 88 as shown in FIG. 5 for receiving the blunt end of an introducer shaft as will be described. The plug is preferably placed toward the distal end of the area enclosed by the cuff 80. A shallow axial passage 90 on the surface of the plug 86 is open to the lumen 60 at each end. While each end of the plug 86 is cylindrical in shape with a relatively tight fit with the interior walls of the lumen, the central part of the plug is provided with a partial girdling recess 92 as shown best in FIG. 3. The purpose of this recess 92 relates to the installation of the plug 86 near the distal end of the lumen. The recess makes it easier to introduce the plug into the lumen. Once the plug is properly positioned, a silicon glue (RTV) is introduced into the cavity 92 to fill the cavity and lock the plug 86 securely in place.

The lumen 60, as described above, opens to the distal end of the catheter. Side opening ports 94 are provided below the cuff sleeve 84 to allow perfusion fluid to escape in the event the end of the lumen is closed by inadvertent contact with a body part. The lumen, however, also is open to the interior of the cuff 80 by side ports 96 at the proximal end of the cuff and at the distal end through opposed ports 98 and 100 shown in FIG. 2. The ports 96,98 and 100 are proportioned in diameter to provide the described inflation pressure in the cuff during the use of the catheter.

Figure 7:
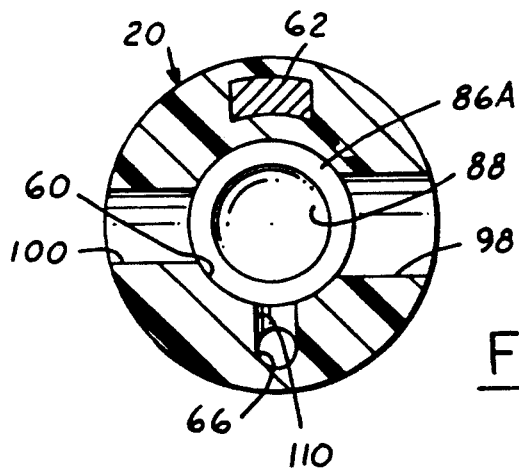
FIG. 7, a section on line 7—7 of FIG. 6.

In FIGS. 6 and 7, a modification is illustrated in which the same reference characters are applied as in FIG. 2 for the same parts. The broken circle in FIG. 6 and the sectional view on line 7—7 of FIG. 6 show a short radial passage 110 extending from the pressure monitoring passage 66 to the lumen 60 within the area covered by the cuff 80. Thus, the pressure being monitored in passages 28 and 66 will approximate the pressure at the distal end (intra-vessel pressure) in normal operation and intra-cuff pressure should the tip be occluded.

In this embodiment in FIGS. 6 and 7, the passage 90 (FIGS. 3 and 4) is eliminated, thus presenting a modified solid plug 86A.

IN THE OPERATION of the described catheter, the first step in the use is the introduction of the catheter into a heart chamber. This is preferably accomplished by the use of an introducer shaft 40 having the hub elements 44,46 and 50. This shaft 40 is projected into the lumen 60 of the catheter and moved down so that the blunt end 42 contacts the hollowed recess 88 of the plug 86. Pressure is then applied to the hub element 44 to stretch out the catheter tube and the tapered element 50 is introduced into the catheter stylet 48 in what is referred to as a slip-lock connection. This tensioning of the catheter stiffens it for the introduction phase.

Once the distal end of the catheter is moved through the wall of the body element together with the deflated cuff, the introducer shaft may be released from the hub 22-48 and withdrawn. The catheter is now ready for connection to a perfusion system. The hub 30 of the pressure monitor line may then be connected to a pressure monitor system.

The recess 88 is provided better to translate the axial force created by the introducer shaft in stretching (tensioning as above) toward the distal tip. The distance between the side ports 96 and the plug 86 is provided so that the introducer end 42 will not escape from the lumen into the cuff should the end of the catheter buckle unexpectedly during the introduction procedure.

What is claimed is:

1. A perfusion catheter which is to be used for introduction into a body cavity comprising:
   (a) a proximal end for introduction of fluid,
   (b) a distal end for introduction into a body cavity,
   (c) a connecting tube between said proximal and distal ends comprised of a flexible material having a central lumen connecting said ends,
   (d) an inflatable cuff enclosing part of said tube adjacent the distal end of the catheter and sealed at each end of said tube,
   (e) a non-removable lumen plug in said central lumen positioned axially within that part of said tube enclosed by said cuff and between the ends of said cuff,
   (f) respective openings in said lumen within and at the proximal and distal ends of said cuff to allow flow from said lumen through said cuff to the distal end of said lumen, and means distally of said cuff to restrict the flow through said cuff to create inflating pressure in said cuff.

2. A perfusion catheter which is to be used for introduction into a body cavity comprising:
   (a) a proximal end for introduction of fluid,
   (b) a distal end for introduction into a body cavity,
   (c) a connecting tube between said proximal and distal ends comprised of a flexible material having a central lumen connecting said ends,
   (d) an inflatable cuff enclosing part of said tube adjacent the distal end of the catheter and sealed at each end on said tube,
   (e) a lumen plug in said central lumen positioned within that part of said tube enclosed by said cuff,
   (f) one or more radial openings in said central lumen open to the interior of said cuff including one or more first openings on the proximal side of said plug, and one or more second openings on the distal end of said plug, said second openings having an effective area less than the effective area of the first openings to create a balloon inflating pressure during flow through said lumen on opposite ends of said plug.

3. A perfusion catheter which is to be used for introduction into a body cavity comprising:
   (a) a proximal end for introduction of fluid,
   (b) a distal end for introduction into a body cavity,
   (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more openings in said lumen within said cuff to admit lumen fluid into said cuff, and means restricting the flow of lumen fluid distally of said plug to create an inflating pressure in said cuff, said central lumen having formed therein, on the proximal side of said plug and within said cuff, first opposed holes opening to the interior of said cuff, and said lumen having formed therein, on the distal side of said plug and within said cuff, opposed second holes opening from the interior of said cuff, at least one of said second holes having a restricted area to cause inflating pressure in said cuff during flow through said lumen.

4. A perfusion catheter which is to be used for introduction into a body cavity comprising:

(a) a proximal end for introduction of fluid, (b) a distal end for introduction into a body cavity, (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more openings in said lumen within said cuff to admit lumen fluid into said cuff, and means restricting the flow of lumen fluid distally of said plug to create an inflating pressure in said cuff, said plug having a restricted axial by-pass passage from end to end to allow limited flow past said plug and within said cuff to the distal end of said lumen.

5. A perfusion catheter which is to be used for introduction into a body cavity comprising:

(a) a proximal end for introduction of fluid, (b) a distal end for introduction into a body cavity, (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more openings in said lumen within said cuff to admit lumen fluid into said cuff, and means restricting the flow of lumen fluid distally of said plug to create an inflating pressure in said cuff, said one or more openings from said lumen to said cuff resulting in a flushing flow through said cuff to prevent stagnation within said cuff, and an introducer shaft to be projected into said lumen with a distal end against said plug to assist in thrusting said catheter into a body vessel.

6. A perfusion catheter which is to be used for introduction into a body cavity comprising:

(a) a proximal end for introduction of fluid, (b) a distal end for introduction into a body cavity, (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more openings in said lumen within said cuff to admit lumen fluid into said cuff, and means restricting the flow of lumen fluid distally of said plug to create an inflating pressure in said cuff, (g) an introducer shaft projectible into said lumen having a distal end to contact said plug and apply endwise pressure to the distal end of said catheter to assist in thrusting said catheter into a body vessel, said introducer shaft having a blunt distal end and said plug having a recess in the proximal end to locate said blunt end of said introducer shaft as axial pressure is applied to the plug.

7. A perfusion catheter which is to be used for introduction into a body cavity comprising:

(a) a proximal end for introduction of fluid, (b) a distal end for introduction into a body cavity, (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more openings in said lumen within said cuff to admit lumen fluid into said cuff, and means restricting the flow of lumen fluid distally of said plug to create an inflating pressure in said cuff, (g) an introducer shaft projectible into said lumen having a distal end to contact said plug and apply endwise pressure to the distal end of said catheter to assist in thrusting said catheter into a body vessel, said catheter having a connector hub at a proximal end and said introducer shaft having a slip-lock hub at a proximal end to insert into said connector hub to be retained during insertion of said catheter.

8. A perfusion catheter which is to be used for introduction into a body cavity comprising:

(a) a proximal end for introduction of fluid, (b) a distal end for introduction into a body cavity, (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more openings in said lumen within said cuff to admit lumen fluid into said cuff, and means restricting the flow of lumen fluid distally of said plug to create an inflating pressure in said cuff, said central lumen having a first opening at the distal end of said central lumen in the tip end of said catheter, and a side port formed in said distal end of said catheter distally of said cuff, said side port being in communication with said central lumen to allow flow to a vessel in the event the first opening is occluded.

9. A perfusion catheter which is to be used for introduction into a body cavity comprising:

(a) a proximal end for introduction of fluid, (b) a distal end for introduction into a body cavity, (c) a connecting tube between said proximal and distal ends comprised of a flexible material having a central lumen connecting said ends, (d) an inflatable cuff enclosing part of said tube adjacent the distal end of the catheter and sealed at each end on said tube, (e) a lumen plug in said central lumen positioned within that part of said tube enclosed by said cuff, (f) one or more radial openings in said central lumen open to the interior of said cuff including one or more first openings on the proximal side of said plug, and one or more second openings on the distal end of said plug, said second openings having an effective area less than the effective area of the first openings to create a balloon inflating pressure during flow through said lumen on opposite ends of said plug, and a pressure monitoring lumen for connection to a pressure monitor parallelling the central lumen and having an open end at the distal end of said catheter and a port adjacent a second opening of said central lumen in the tip of said catheter to communicate with the interior of said cuff.

10. A perfusion catheter as defined in claim 9 in which said pressure monitoring lumen is spliced into said connecting tube distally of said proximal end and a band encircles said connecting tube and said monitoring tube at the splice location.

11. A perfusion catheter as defined in claim 9 in which passage means located beyond the distal end of said lumen plug and within the distal end of said cuff communicates with said pressure monitoring lumen to monitor pressure in said cuff.

12. A perfusion catheter as defined in claim 9 in which a port at the distal end of said monitoring passage connects said passage with the interior diameter of the catheter body under said cuff to obtain monitoring of pressure within said cuff as well as within a body chamber into which the distal end of the catheter is inserted, in situations of tip occlusion and normal operation, respectively.

* * * * *